(12) United States Patent
Zhou et al.

(10) Patent No.: US 10,205,466 B2
(45) Date of Patent: Feb. 12, 2019

(54) ELECTRONIC DEVICE WITH FLEXIBLE PROCESSING OF COMPRESSIVE SENSING SAMPLES

(71) Applicant: MEDIATEK INC., Hsin-Chu (TW)

(72) Inventors: Qiang Zhou, San Jose, CA (US); Hua Wang, San Francisco, CA (US); Yun-Shiang Shu, Hsinchu County (TW); Bao-Chi Peng, Taipei (TW)

(73) Assignee: MEDIATEK INC., Hsin-Chu (TW)

( * ) Notice: Subject to any disclaimer, the term of this patent is extended or adjusted under 35 U.S.C. 154(b) by 0 days.

(21) Appl. No.: 15/830,000

(22) Filed: Dec. 4, 2017

(65) Prior Publication Data

US 2018/0183461 A1 Jun. 28, 2018

Related U.S. Application Data

(60) Provisional application No. 62/437,752, filed on Dec. 22, 2016.

(51) Int. Cl.
*H03M 7/34* (2006.01)
*H03M 7/30* (2006.01)
*A61B 5/00* (2006.01)

(52) U.S. Cl.
CPC ......... *H03M 7/3088* (2013.01); *A61B 5/0002* (2013.01); *A61B 5/7232* (2013.01)

(58) Field of Classification Search
CPC ..... H03M 7/3088; H03M 7/30; A61B 5/7232; A61B 5/002; A61B 5/00

(Continued)

(56) References Cited

U.S. PATENT DOCUMENTS 7,864,077 B2 * 1/2011 Cormode ............... H03M 7/30
341/50
8,396,310 B1 * 3/2013 Kadambe ............. G06K 9/6244
348/404.1

(Continued)

FOREIGN PATENT DOCUMENTS

CN 101795501 B 8/2012
CN 103107815 B 3/2016
TW 201126912 A1 8/2011

OTHER PUBLICATIONS

Chen, Compressive Wireless Pulse Sensing, 2015 International Conference on Collaboration Technologies and Systems (CTS).

(Continued)

*Primary Examiner* — Jean B Jeanglaude
(74) *Attorney, Agent, or Firm* — Winston Hsu

(57) ABSTRACT

An electronic device has a transmit circuit and a processing circuit. The processing circuit outputs a first portion of compressive sensing (CS) samples corresponding to a signal segment to another electronic device via the transmit circuit, and selectively outputs a second portion of the CS samples corresponding to the signal segment to another electronic device via the transmit circuit according to a response of another electronic device. In this way, a balance between the compression ratio and the reconstruction quality/speed can be achieved. Moreover, the signal reconstruction performed at the processing circuit may employ a multi-resolution/multi-scale reconstruction scheme to achieve a balance between the dictionary size and the reconstruction quality/speed, and/or may employ a multi-stage reconstruction scheme to achieve a balance between the reconstruction algorithm control setting and the reconstruction quality/speed. In addition, dictionary weighting, online dictionary update, and/or point constraints may be used to improve the reconstruction quality.

20 Claims, 11 Drawing Sheets

(58) Field of Classification Search
USPC .................. 341/118, 50, 51; 375/260, 239
See application file for complete search history.

(56) References Cited

U.S. PATENT DOCUMENTS

| | | | | |
|---|---|---|---|---|
| 8,547,258 B2* | 10/2013 | Sestok | ................ | H03M 7/3062 |
| | | | | 341/118 |
| 8,774,294 B2* | 7/2014 | Shental | ............... | H04L 25/0202 |
| | | | | 375/260 |
| 8,804,811 B2* | 8/2014 | Muqaibel | ........... | H04B 1/71637 |
| | | | | 375/239 |
| 9,548,758 B2* | 1/2017 | Marzetta | ................. | H03M 7/30 |

OTHER PUBLICATIONS

Gangopadhyay, Compressed Sensing Analog Front-End for Bio-Sensor Applications, IEEE Journal of Solid-State Circuits, pp. 426-438, vol. 49, No. 2. Feb. 2014.

Kuo, A 1V 9uA Analog Front End with Compressed Sensing for Electrocardiogram Monitoring, IEEE Asian Solid-State Circuits Conference, Nov. 9-11, 2015.

* cited by examiner

ELECTRONIC DEVICE WITH FLEXIBLE PROCESSING OF COMPRESSIVE SENSING SAMPLES

CROSS REFERENCE TO RELATED APPLICATIONS

This application claims the benefit of U.S. provisional application No. 62/437,752, filed on Dec. 22, 2016 and incorporated herein by reference.

BACKGROUND

The disclosed embodiments of the present invention relate to compressive sensing (CS), and more particularly, to an electronic device with flexible processing of CS samples.

Wearable sensor devices are increasingly employed in medical monitoring, where high energy efficiency, small form factor, multi-signal sensing capability and wireless communication capability are essential. A typical wireless bio-sensor system consists of bio-sensor nodes (e.g., wearable bio-sensor devices) that transmit information to a data aggregator (e.g., a smartphone) that receives and processes the bio-sensor output data. One restriction imposed on the wearable bio-sensor devices is power consumption. These wearable bio-sensor devices need to operate for a reasonable amount of time to avoid frequent battery replacement/charging. In general, the majority of the power is consumed by a transmit (TX) circuit (particularly, a power amplifier (PA) of the TX circuit). One solution to reduce the power consumption is to reduce the data rate. Compressive sensing (CS) is a signal processing technique that exploits sparsity for commensurate power savings by enabling alias-free sub-Nyquist-rate acquisition. Hence, CS is very appealing to low-power wearable bio-sensor devices. To achieve good compression ratio in CS framework, it is important to find a suitable basis. However, a typical fixed basis such as wavelet-based CS design only gives a compression ratio (CR) of 2-2.5 if the required signal-to-noise ratio (SNR) is 20 dB or above. In addition, a reconstruction algorithm employed by the typical data aggregator (e.g., smartphone) needs to run till full recovery, and early stop due to computational constraints reduces the reconstruction quality significantly. Moreover, the reconstruction algorithm employed by the typical data aggregator (e.g., smartphone) lacks capability to handle different types of impairments.

Thus, there is a need for a flexible bio-sensing system design that provides a high compression ratio for various bio-signal types and is able to handle different types of impairments.

SUMMARY

In accordance with exemplary embodiments of the present invention, an electronic device with flexible processing of CS samples is proposed to solve the above-mentioned problem.

According to a first aspect of the present invention, an exemplary electronic device is disclosed. The exemplary electronic device includes a transmit circuit and a processing circuit. The processing circuit is arranged to output a first portion of compressive sensing (CS) samples corresponding to a signal segment to another electronic device via the transmit circuit, and is further arranged to selectively output a second portion of the CS samples corresponding to the signal segment to said another electronic device via the transmit circuit according to a response of said another electronic device.

According to a second aspect of the present invention, an exemplary electronic device is disclosed. The exemplary electronic device includes a receive circuit and a processing circuit. The processing circuit is arranged to receive a first portion of compressive sensing (CS) samples corresponding to a signal segment from another electronic device via the receive circuit, and is further arranged to selectively request a second portion of the CS samples corresponding to the signal segment from said another electronic device according to a reconstruction quality requirement.

According to a third aspect of the present invention, an exemplary electronic device is disclosed. The exemplary electronic device includes a storage device and a processing circuit. The storage device is arranged to store a plurality of dictionaries, including at least one first-stage dictionary and at least one second-stage dictionary. The processing circuit is arranged to perform a first-stage reconstruction of a data group according to compressive sensing (CS) samples corresponding to a signal segment and a first-stage dictionary selected from said at least one first-stage dictionary, and is further arranged to selectively perform a second-stage reconstruction of the data group according to the CS samples corresponding to the signal segment, the first-stage dictionary, and a second-stage dictionary selected from said at least one second-stage dictionary.

According to a fourth aspect of the present invention, an exemplary electronic device is disclosed. The exemplary electronic device includes a transmit circuit, a processing circuit, and a feature point detection circuit. The processing circuit is arranged to perform compressive sensing (CS) to generate CS samples corresponding to a signal segment, and output at least a portion of the CS samples corresponding to the signal segment to another electronic device via the transmit circuit. The feature point detection circuit is arranged to detect at least one feature point sample associated with at least one feature point of the signal segment, and output at least one feature point sample to said another electronic device via the transmit circuit.

According to a fifth aspect of the present invention, an exemplary electronic device is disclosed. The exemplary electronic device includes a receive circuit and a processing circuit. The processing circuit is arranged to receive at least a portion of compressive sensing (CS) samples corresponding to a signal segment and at least one feature point sample associated with at least one feature point of the signal segment from another electronic device via the receive circuit, and perform reconstruction of a data group according to said at least a portion of the CS samples and said at least one feature point sample.

These and other objectives of the present invention will no doubt become obvious to those of ordinary skill in the art after reading the following detailed description of the preferred embodiment that is illustrated in the various figures and drawings.

DETAILED DESCRIPTION

Certain terms are used throughout the description and following claims to refer to particular components. As one skilled in the art will appreciate, manufacturers may refer to a component by different names. This document does not intend to distinguish between components that differ in name but not function. In the following description and in the claims, the terms "include" and "comprise" are used in an open-ended fashion, and thus should be interpreted to mean "include, but not limited to . . . ". Also, the term "couple" is intended to mean either an indirect or direct electrical connection. Accordingly, if one device is electrically connected to another device, that connection may be through a direct electrical connection, or through an indirect electrical connection via other devices and connections.

There are many tradeoffs in the system design. For example, the compression ratio, the dictionary size, and the reconstruction algorithm setting all contribute to quality and speed. A higher compression ratio leads to lower quality and faster processing speed, and a lower compression ratio leads to higher quality and slower processing speed. A smaller dictionary size leads to lower quality and faster processing speed, and a larger dictionary size leads to higher quality and slower processing speed. A reconstruction algorithm that is early stopped leads to lower quality and faster processing speed, and a reconstruction algorithm that runs till full recovery leads to higher quality and slower processing speed. To achieve a balance between the compression ratio and the reconstruction quality/speed, the present invention proposes a variable rate transmission scheme. To achieve a balance between the dictionary size and the reconstruction quality/speed, the present invention proposes a multi-resolution/multi-scale reconstruction scheme. To achieve a balance between the reconstruction algorithm setting and the reconstruction quality/speed, the present invention proposes a multi-stage reconstruction scheme. Moreover, to improve the reconstruction quality, the present invention further proposes using dictionary weighting, performing an online dictionary update, and/or adding point constraints. Further details of these innovative signal processing strategies are described hereinafter with reference to the accompanying drawings. In one exemplary design, a compressive sensing (CS) based data processing system may employ one proposed signal processing strategy to achieve good performance. In another exemplary design, a CS based data processing system may employ a combination of different proposed signal processing strategies to achieve better performance.

Figure 1:
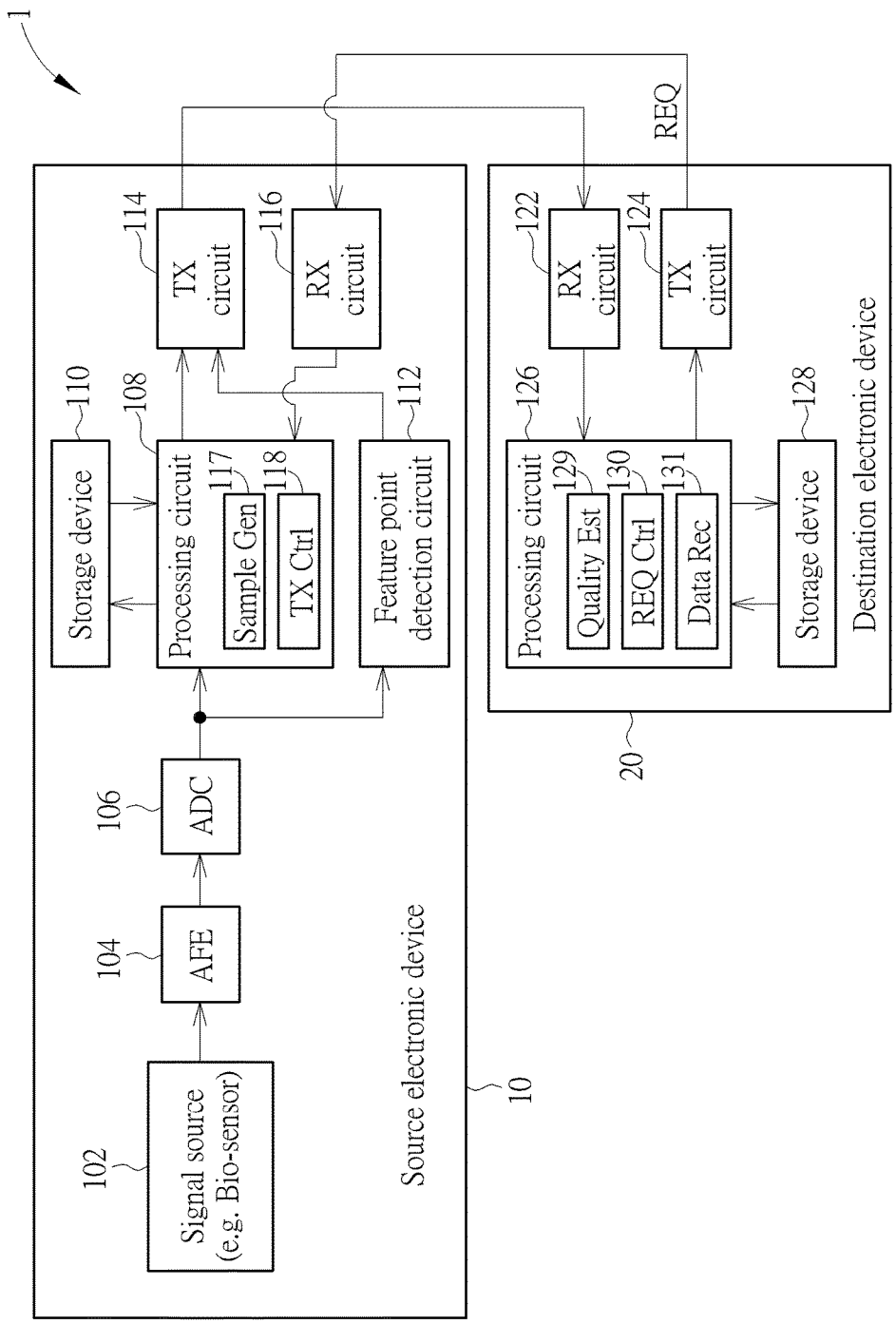
FIG. 1 is a diagram illustrating a compressive sensing based data processing system according to an embodiment of the present invention.

FIG. 1 is a diagram illustrating a CS based data processing system according to an embodiment of the present invention. By way of example, but not limitation, the CS based data processing system 1 may be a wireless bio-sensing system. As shown in FIG. 1, the CS based data processing system 1 includes a source electronic device (e.g., wearable bio-sensor device) 10 and a destination electronic device (e.g., smartphone) 20. The source electronic device 10 includes a signal source (e.g., bio-sensor) 102, an analog front-end (AFE) 104, an analog-to-digital converter (ADC) 106, a processing circuit 108, a storage device 110, a feature point detection circuit 112, a transmit (TX) circuit 114, and a receive (RX) circuit 116. The processing circuit 108 may be configured to have a plurality of sub-blocks such as a sample generation block (denoted by "Sample Gen") 117 and a transmit control block (denoted by "TX Ctrl") 118. The destination electronic device 20 includes a receive (RX) circuit 122, a transmit (TX) circuit 124, a processing circuit 126, and a storage device 128. The processing circuit 126 may be configured to have a plurality of sub-blocks such as a quality estimation block (denoted by "Quality Est") 129, a data request control block (denoted by "REQ Ctrl") 130 and a data reconstruction block (denoted by "Data Rec") 131. In this embodiment, only one signal source 102 is implemented in the source electronic device 10. Alternatively, the source electronic device 10 may be a multi-sensor device configured to have more than one signal source (e.g., bio-sensor) 102.

For clarity and simplicity, the following assumes that the signal source 102 is a bio-sensor used for generating a bio-signal to be compressed and transmitted. For example, the bio-signal may be an electrocardiogram (ECG) signal, a photoplethysmogram (PPG) signal, or arterial blood pressure (ABP) signal. However, these are for illustrative purposes only, and are not meant to be limitations of the present invention.

Since the bio-signal is an analog signal, it is pre-processed by AFE 104 and then fed into the ADC 106. For example, AFE 104 may include a low-noise amplifier (LNA). In this embodiment, the sample generation block 117 is configured to perform compressive sensing in a digital domain. Hence, the ADC 106 performs analog-to-digital conversion upon the bio-signal to generate signal samples (e.g., ECG signal samples) according to a sampling rate defined by an ADC clock rate. The sample generation block 117 performs digital compressive sensing upon the signal samples to generate CS samples. The digital compressive sensing is used to compress N input samples, $X=[x_1 \ldots x_N]^T$, into M output samples, $Y=[y_1 \ldots y_M]^T$, where the compression ratio (CR) equals N/M. The digital compressive sensing may be represented using a simple matrix equation $Y=\Phi X$, where an uncompressed input vector X of size N multiplied by a measurement matrix $\Phi$ of size M×N produces a measurement vector Y of size M. Typically, $\Phi$ is an array of independent and identically distributed random numbers, thus Y is a vector of random linear projections of X on $\Phi$ which contains all the information for reconstructing the original signal X with high probability. The compressive sensing (i.e., random sampling) at the sensor node can compress signal samples to reduce the data to be transmitted to the data aggregator (e.g., smartphone), thus reducing the power dissipation in the sensor node.

In one exemplary design, the source electronic device (e.g., bio-sensor device) 10 employs a variable rate transmission scheme to achieve a balance between the compression ratio and the reconstruction quality/speed. The TX control block 118 controls CS sample transmission in a mega block basis, where a mega block is ready when the number of CS samples gathered from digital compressive sensing reaches a pre-set size. In other words, a certain amounts of signal segment of the bio-signal is sampled at the ADC 106 to produce a certain size data group composed of signal samples, and the data group is compressed by digital compressive sensing with a predetermined CR at the sample generation block 117 to produce a mega block. The mega block based operation can reduce the repeated wakeup and setup time, and can save power due to continuous transmitting.

In accordance with the proposed variable rate transmission scheme, the TX control block 118 of the source electronic device 10 outputs a portion of CS samples in a mega block (which corresponds to a signal segment of the bio-signal within a time window) to the destination electronic device 20 via the TX circuit 114, and selectively outputs another portion of the CS samples in the same mega block (which corresponds to the same signal segment of the bio-signal within the same time window) to the destination electronic device 20 via the TX circuit 114 according to a response of the destination electronic device 20. In other words, the TX rate of one mega block varies depending upon the feedback from the destination electronic device 20. Since the TX rate of one mega block is variable, the effective compression ratio between the uncompressed data of the bio-signal and the compressed data actually transmitted from the source electronic device 10 to the destination electronic device 20 is variable.

Figure 2:
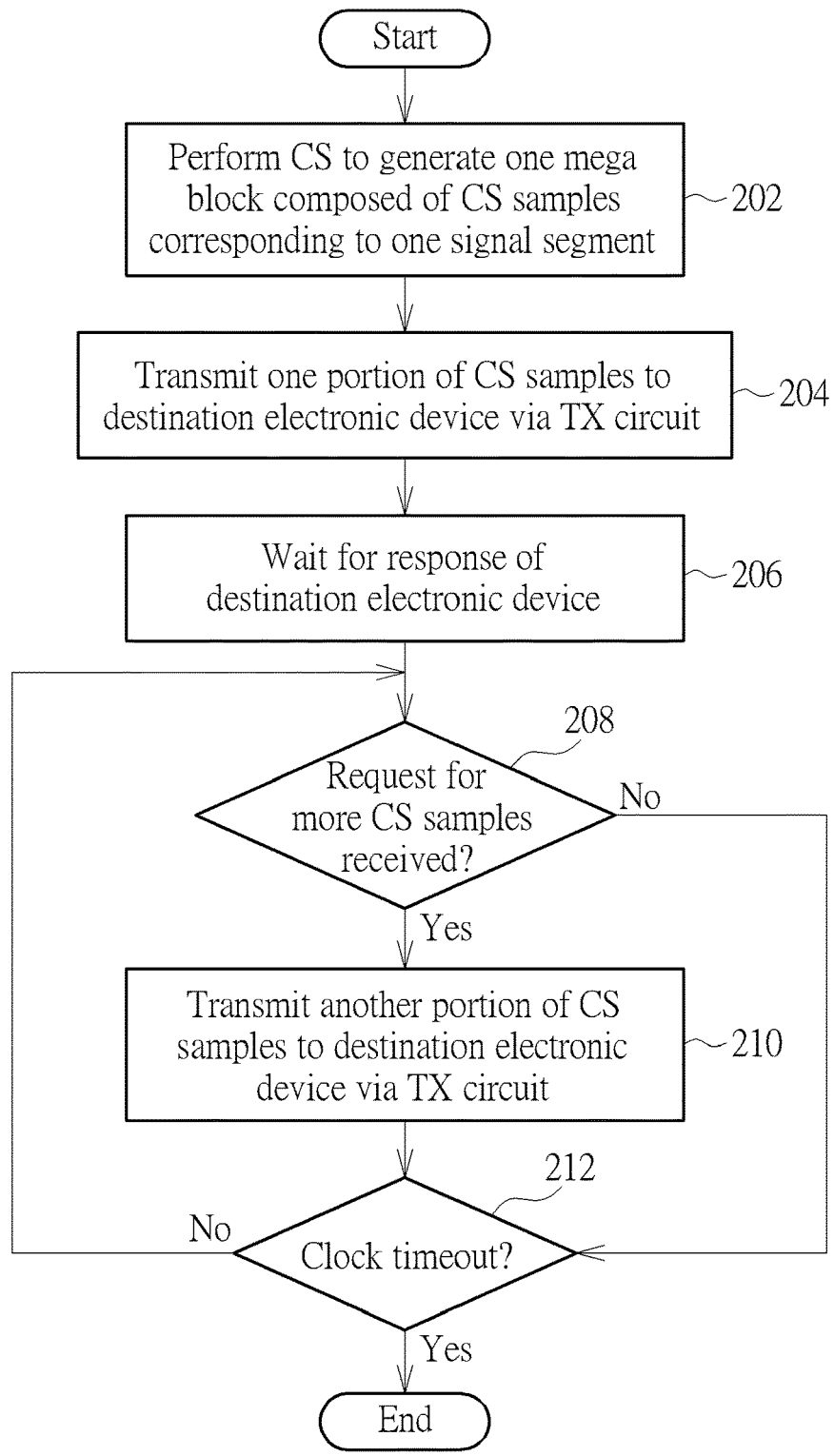
FIG. 2 is a flowchart illustrating a method of adaptively controlling a TX rate of one mega block according to an embodiment of the present invention.

FIG. 2 is a flowchart illustrating a method of adaptively controlling a TX rate of one mega block according to an embodiment of the present invention. For example, the method shown in FIG. 2 may be performed by the processing circuit 108 that includes the sample generation block 117 and the TX control block 118. Further, provided that the result is substantially the same, the steps are not required to be executed in the exact order shown in FIG. 2. As mentioned above, the sample generation block 117 performs compressive sensing upon signal samples generated by sampling the analog bio-signal, and obtains CS samples that are randomly selected from the signal samples according to a predetermined CR (e.g., CR=2). Hence, at step 202, the sample generation block 117 performs compressive sensing to generate one mega block composed of CS samples corresponding to one signal segment of the bio-signal. The storage device 110 may be configured to have one or more buffers allocated therein for buffering CS samples. For example, assuming that the compressive sensing adopts a particular CR and the mega block size is set by $S_{MB}$, one mega block composed of $S_{MB}$ CS samples is ready in the storage device 110 after a data group composed of $S_{MB}*CR$ signal samples generated from sampling a signal segment of the bio-signal within a time window is processed by compressive sensing (i.e., random sampling) at the sample generation block 117.

At step 204, the TX control block 118 only outputs a first portion of CS samples in a current mega block to the destination electronic device 20 via the TX circuit 114. When the size of the transmitted first portion of CS samples in one mega block is equal to $$\frac{1}{A} \cdot S_{MB},$$

the effective compression ratio between the uncompressed data of the bio-signal and the compressed data actually transmitted from the source electronic device 10 to the destination electronic device 20 is equal to A·CR. It should be noted that the remaining portion of CS samples in the current mega block is kept in the storage device 110 without being transmitted to the destination electronic device 20 at this moment.

At step 206, the TX control block 118 waits for a response of the destination electronic device 20. At step 208, the TX control block 118 checks if a request REQ for more CS samples of the current mega block is received from the destination electronic device 20 via the RX circuit 116. If the request REQ is not received, the TX control block 118 checks if a timeout criterion is met (step 212). When the timeout criterion is met, it means the TX control block 118 is allowed to apply variable rate transmission to a next mega block. Hence, if the timeout criterion is not met yet, the flow proceeds with step 208 to keep checking if a request REQ for more CS samples is received. If the timeout criterion is met, the variable rate transmission applied to the current mega block is completed and the current mega block is cleared from the storage device 110.

If the request REQ is received at step 208, the TX control block 118 outputs a second portion of CS samples in the current mega block to the destination electronic device 20 via the TX circuit 114. In a case where the variable rate transmission scheme supports only two TX rates, the second portion of CS samples in the current mega block is the remaining portion of CS samples in the current mega block that are currently buffered in the storage device 110. Hence, the effective compression ratio between the uncompressed data of the bio-signal and the compressed data actually transmitted from the source electronic device 10 to the destination electronic device 20 is equal to CR. In addition, the storage device 110 may be configured to have a first buffer and a second buffer, wherein the first portion of CS samples in the current mega block is stored into the first buffer, and the second portion of CS samples in the current mega block is stored into the second buffer.

In another case where the variable rate transmission scheme supports more than two TX rates, the second portion of CS samples in the current mega block is a fraction of the remaining portion of CS samples in the current mega block that is currently buffered in the storage device 110. When the size of the transmitted second portion of CS samples in one mega block is equal to $$\frac{1}{B} \cdot S_{MB},$$

the effective compression ratio between the uncompressed data of the bio-signal and the compressed data actually transmitted from the source electronic device 10 to the destination electronic device 20 becomes $$\frac{A \cdot B}{A+B} \cdot CR.$$

In addition, the storage device 110 may be configured to have more than two buffers, wherein different portions of CS samples in the current mega block are stored into different buffers, respectively.

The RX circuit 122 of the destination electronic device 124 receives CS samples of one mega block transmitted from the TX circuit 114 of the source electronic device 10, and the data reconstruction block 131 performs reconstruction of a data group according to the received CS samples of one mega block to obtain reconstructed signal samples of the data group. As mentioned above, the digital compressive sensing performed by the processing circuit 108 is used to compress N input samples, $X=[x_1 \ldots x_N]^T$, into M output samples, $Y=[y_1 \ldots y_M]^T$, where the compression ratio (CR) equals N/M. Suppose the input X is k-sparse in an N×N sparse basis (or a dictionary) $\Psi$, so that $X=\Psi S$, where S is a coefficient vector of size N containing only k non-zero coefficients k<<N. When the sparse basis $\Psi$ and the measurement matrix $\Phi$ are incoherent, accurate reconstruction can be ensured. The digital compressive sensing may be represented using a simple matrix equation $Y=\Phi X$. Since $X=\Psi S$, the matrix equation $Y=\Phi X$ can be reformulated as $Y=\Phi \Psi S$. Since the measurement vector Y, the measurement matrix $\Phi$, and the spars basis (or dictionary) $\Psi$ in the matrix equation $Y=\Phi \Psi S$ are known, the coefficient vector S can be found by using a proper reconstruction/approximation algorithm taking advantage of sparseness of coefficient vector S. After the coefficient vector S is obtained, the reconstructed signal samples $\hat{X}$ can be obtained by multiplying the sparse basis matrix $\Psi$ and the projection coefficients in the coefficient vector S, that is, $\hat{X}=\Psi S$.

As mentioned above, a signal segment of the bio-signal within a time window is sampled at the ADC 106 to produce a data group composed of signal samples, the data group is compressed by compressive sensing at the sample generation block 117 to produce a mega block, and the mega block is fully transmitted or partially transmitted according to the proposed variable rate transmission scheme. In accordance with the proposed variable rate transmission scheme, the data reconstruction block 131 of the destination electronic device 20 receives a portion of CS samples in a mega block (which corresponds to a signal segment of the bio-signal within a time window) from the source electronic device 10 via the receive circuit 122, and the request control block 130 of the destination electronic device 20 selectively requests another portion of the CS samples in the same mega block (which corresponds to the same signal segment of the bio-signal within the same time window) from the source electronic device 10 according to a reconstruction quality requirement performed at the quality estimation block 129 of the destination electronic device 20.

Figure 3:
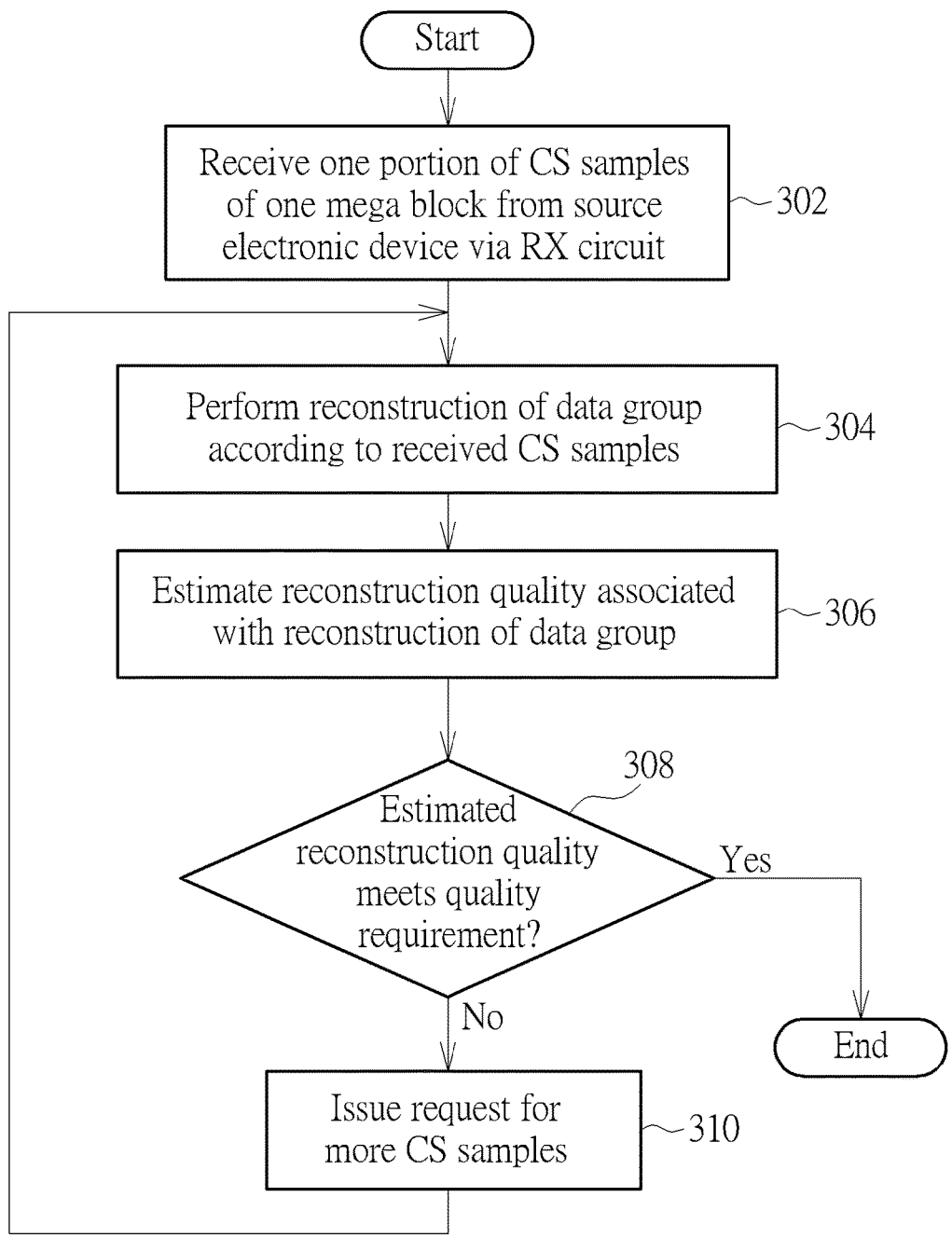
FIG. 3 is a flowchart illustrating a method of adaptively requesting CS samples of one mega block according to an embodiment of the present invention.

FIG. 3 is a flowchart illustrating a method of adaptively requesting CS samples of one mega block according to an embodiment of the present invention. For example, the method shown in FIG. 3 may be performed by the processing circuit 126 that includes the quality estimation block 129, the request control block 130 and the data reconstruction block 131. Further, provided that the result is substantially the same, the steps are not required to be executed in the exact order shown in FIG. 3. At step 302, the data reconstruction block 131 receives the aforementioned first portion of CS samples in the current mega block from the source electronic device 10 via the receive circuit 122. At step 304, the data reconstruction block 131 performs reconstruction of a data group according to the first portion of CS samples in the current mega block, where the current mega block is generated by applying digital compressive sensing to the data group composed of signal samples that are generated by sampling a signal segment of the bio-signal within a time window. At step 306, the quality estimation block 129 estimates reconstruction quality associated with reconstruction of the data group. At step 308, the request control block 130 checks if the estimated reconstruction quality meets the reconstruction quality requirement. If the estimated reconstruction quality does not meet the reconstruction quality requirement, the request control block 130 issues the request REQ for the aforementioned second portion of CS samples in the current mega block (step 310), and the data reconstruction block 131 performs reconstruction again according to the previously received first portion of CS samples in the current mega block and the newly received second portion of CS samples in the current mega block (step 304). If the estimated reconstruction quality meets the reconstruction quality requirement, the request control block 130 does not need to issue the request REQ for more CS samples, and the data request control applied to reconstruction of the current data group is completed.

Figure 4:
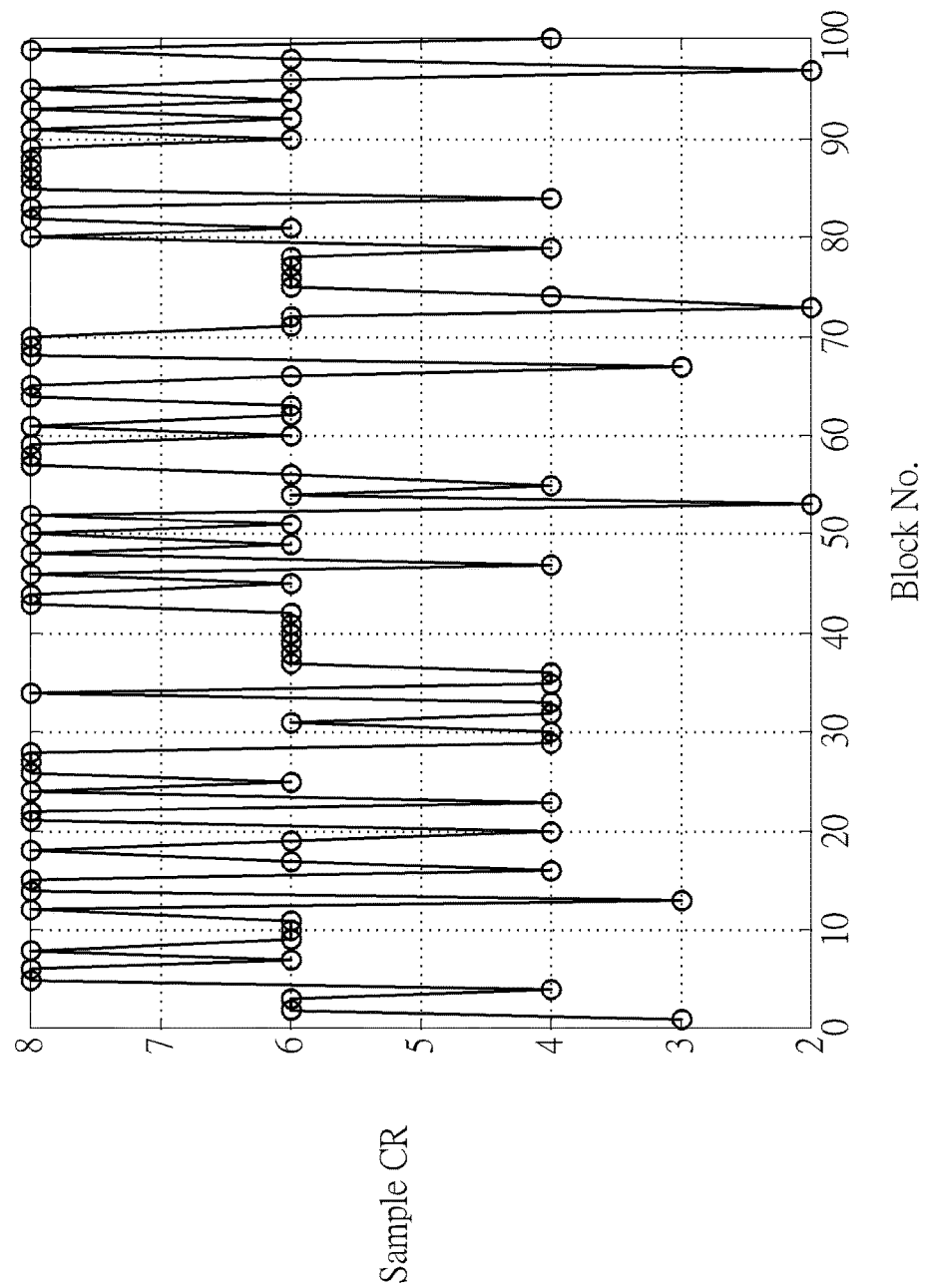
FIG. 4 is a diagram illustrating effective compression ratios of mega blocks improved by a variable rate transmission scheme according to an embodiment of the present invention.

In accordance with the variable rate transmission scheme, the source electronic device 10 adaptively adjusts a TX rate according to the result of reconstruction quality estimation performed at the destination electronic device 20. When the estimated reconstruction quality can meet the reconstruction quality requirement under a condition that only a portion of CS samples in one mega block is transmitted from the source electronic device 10, the effective compression ratio between the uncompressed data of the bio-signal and the compressed data actually transmitted from the source electronic device 10 to the destination electronic device 20 can be larger than the original compression ratio employed by the compressive sensing (e.g., CR=2), as illustrated in FIG. 4. When the variable rate transmission scheme supports a plurality of different TX rates, an effective compression ratio associated with a mega block can be selected from a plurality of different CRs.

When the CR (i.e., N/M) is high, N is much larger than M, the equation $Y=\Phi \Psi S$ is an under-determined system. Since there are more columns than rows, there is more freedom to have matched projection. As a result, the accuracy of CS reconstruction may be poorer for a high CR. As mentioned above, the processing circuit 126 performs reconstruction quality estimation to determine if more CS samples are needed to achieve a more accurate reconstruction result. However, the signal-to-noise ratio (SNR) is based on ground truth, and cannot be measured in an online manner. The present invention proposes estimating the reconstruction quality by performing sparseness check upon coefficients that are found by the reconstruction of the data group (i.e., coefficients in the coefficient vector S found by a reconstruction/approximation algorithm). For example, the sparseness check may include calculating a decay rate of the coefficients and using the calculated decay rate as an indication of the reconstruction quality. When the calculated decay rate is larger than a threshold, it is determined that the reconstruction quality requirement is met. When the calculated decay rate is not larger than the threshold, it is determined that the reconstruction quality requirement is not met.

Figure 5:
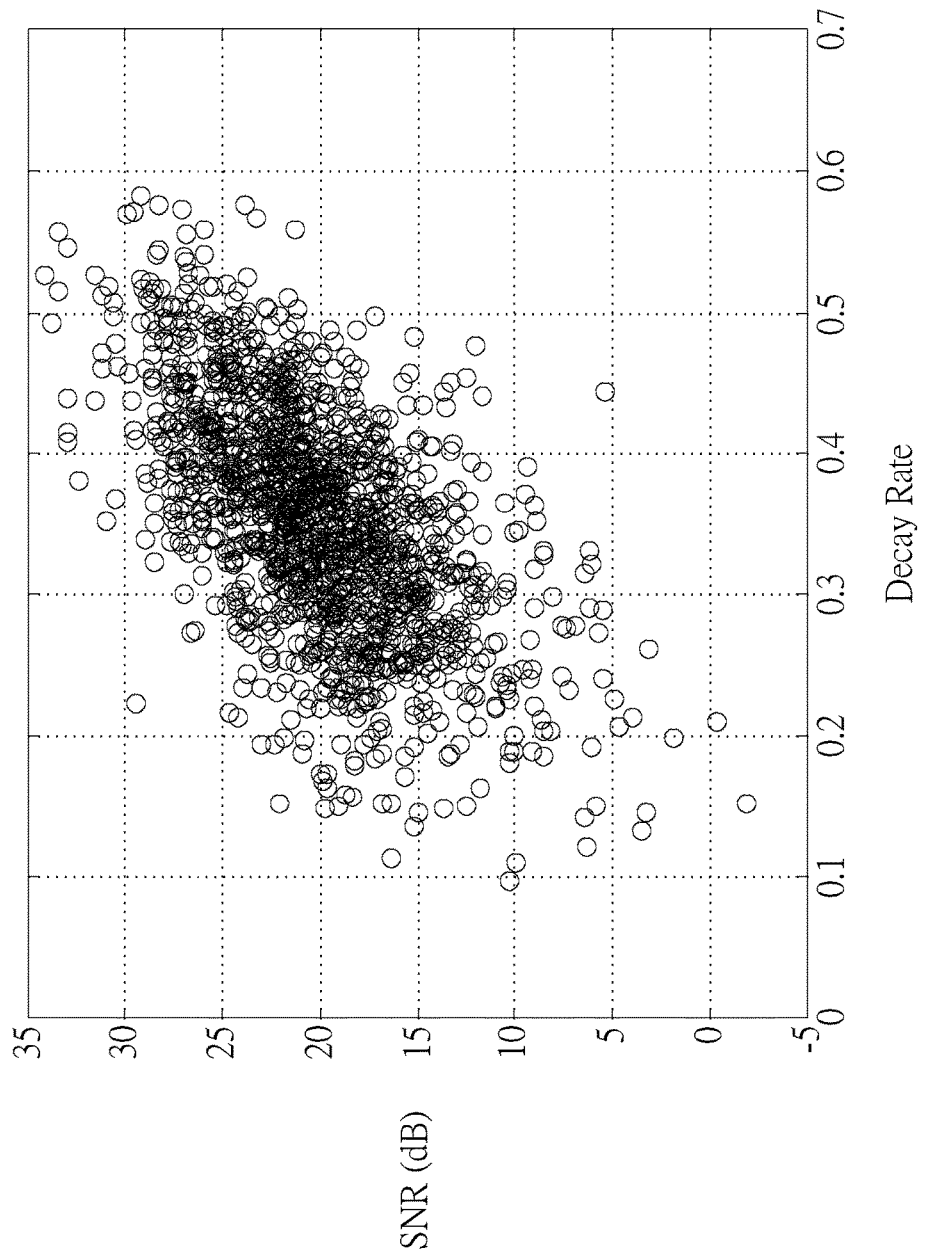
FIG. 5 is a diagram illustrating a relation between a decay rate of coefficients and an SNR of CS reconstruction according to an embodiment of the present invention.

FIG. 5 is a diagram illustrating a relation between a decay rate of coefficients and an SNR of CS reconstruction according to an embodiment of the present invention. As illustrated in FIG. 5, the decay rate is positively correlated to the SNR. In other words, a higher decay rate implies a better SNR, and a lower decay rate implies a worse SNR. Since the decay rate can be calculated in an online manner, the decay rate can be used for reconstruction quality estimation.

Figure 6:
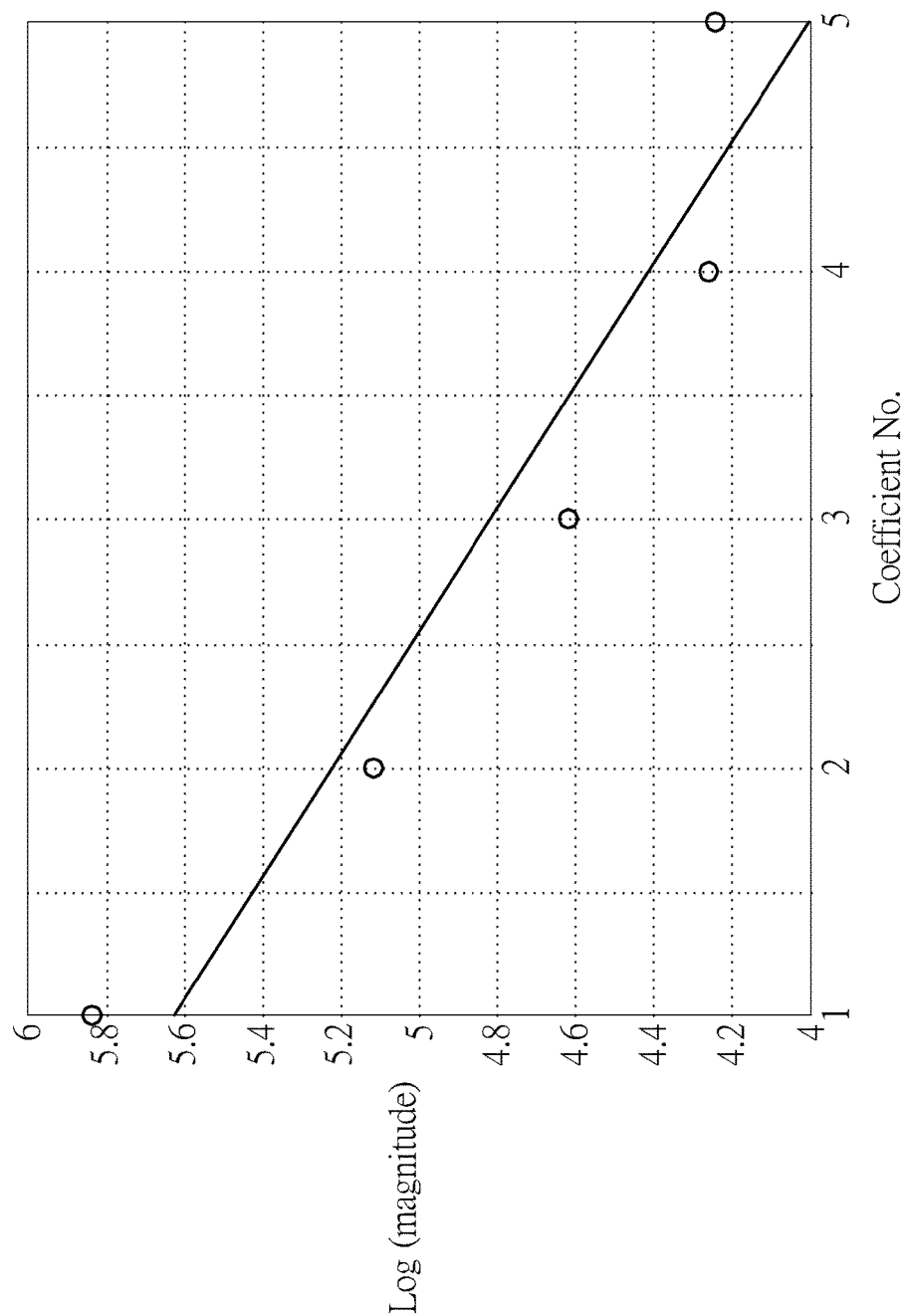
FIG. 6 is a diagram illustrating an example of calculating a decay rate of coefficients according to an embodiment of the present invention.

FIG. 6 is a diagram illustrating an example of calculating a decay rate of coefficients according to an embodiment of the present invention. For clarity and simplicity, only top five non-zero coefficients are illustrated. The coefficient decay is modeled as an exponential function. Hence, the decay rate is approximated using least squares (LS) fitting on logarithms of the magnitude of coefficients. When the calculated decay rate shows a faster decaying behavior, the reconstruction quality is better.

In one exemplary design, the destination electronic device 20 may employ a multi-resolution/multi-scale reconstruction scheme to achieve a balance between the dictionary size and the reconstruction quality/speed. In another exemplary design, the destination electronic device 20 may employ a multi-stage reconstruction scheme to achieve a balance between the reconstruction algorithm control setting and the reconstruction quality/speed. In yet another exemplary design, the destination electronic device 20 may employ a multi-resolution and multi-scale reconstruction scheme to achieve a balance between the dictionary size and the reconstruction quality/speed. In the following, the principle of the multi-resolution and multi-stage reconstruction scheme is detailed. Since a person skilled in the pertinent art should readily understand principles of the multi-resolution reconstruction scheme and the multi-stage reconstruction scheme after reading following paragraphs directed to the multi-resolution and multi-stage reconstruction scheme, further description is omitted for brevity.

Figure 7:
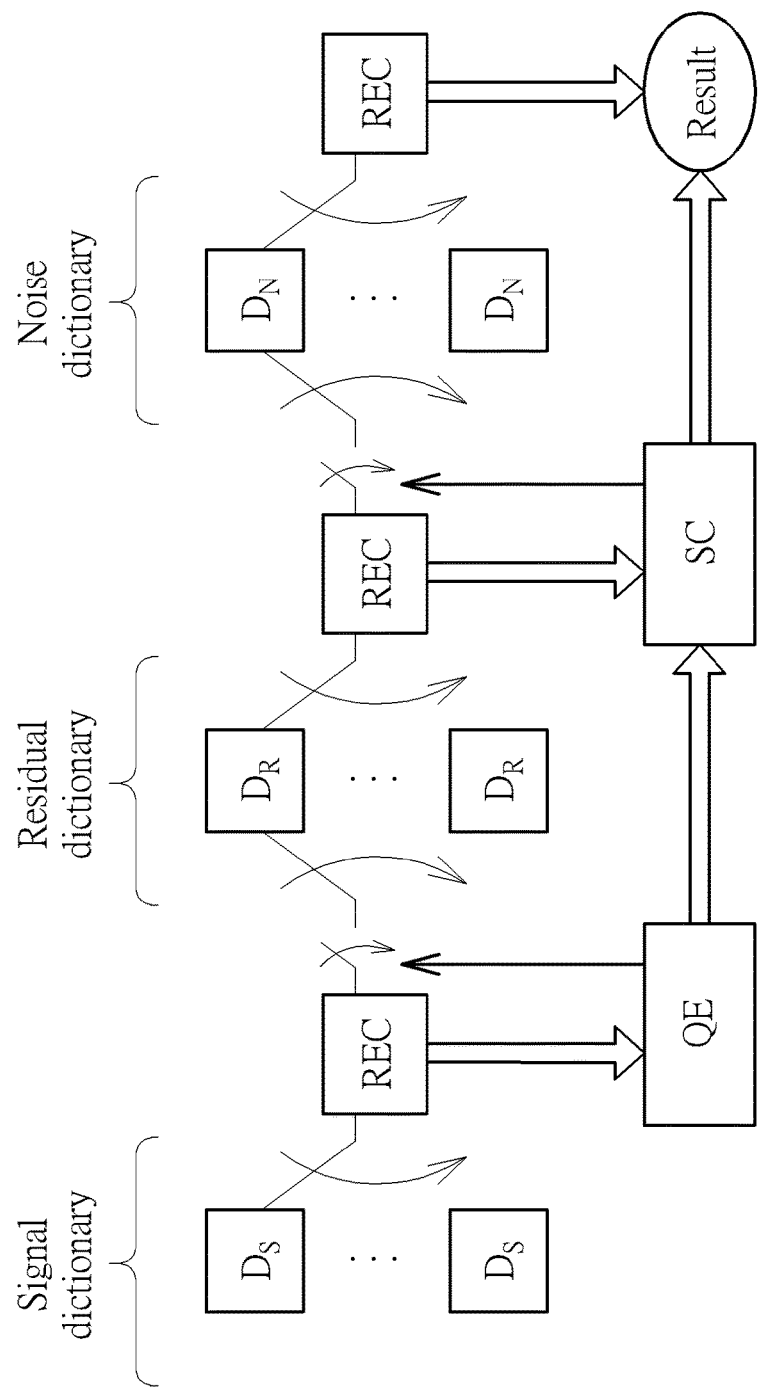
FIG. 7 is a diagram illustrating a multi-resolution and multi-stage reconstruction scheme according to an embodiment of the present invention.

FIG. 7 is a diagram illustrating a multi-resolution and multi-stage reconstruction scheme according to an embodiment of the present invention. Multi-resolution/multi-scale dictionaries (e.g., multi-resolution/multi-scale signal dictionaries $D_S$, multi-resolution/multi-scale residual dictionaries $D_R$, and/or multi-resolution/multi-scale noise dictionaries $D_N$) are needed by the multi-resolution reconstruction scheme. Different types of dictionaries (e.g., a signal dictionary and a residual dictionary, a signal dictionary and a noise dictionary, or a signal dictionary, a residual dictionary and a noise dictionary) are needed by the multi-stage reconstruction scheme. In this embodiment, each of the dictionaries may be a learned dictionary obtained from offline dictionary learning. As mentioned above, the signal samples are compressible in the sparse basis (or dictionary) $\Psi$, such that a signal sample can be represented using a linear combination of a few atoms of the dictionary $\Psi$. The dictionary $\Psi$ can be either based on a mathematical model of the data or can be learned directly from the data. It has been observed that learning a dictionary directly from offline training rather than using a predetermined dictionary (e.g., wavelet dictionary) usually leads to more sparse representation and better reconstruction quality. For example, the ECG signals are not truly sparse in the wavelet domain. As a result, any existing wavelet wave form does not match the ECG signal close enough. Hence, learning a dictionary for ECG signals seems to be a better choice. One benefit of learning a dictionary is that it is sparser in the space spanned by atoms in the dictionary, thus requiring less CS samples to be collected. Another benefit of learning a dictionary is that an over-complete dictionary gives the power of noise reduction, thus allowing a coarse resolution of each CS sample for bit reduction.

The storage device 128 of the destination electronic device 20 is used to store learned dictionaries that are obtained by offline dictionary learning and are later used by online signal reconstruction. The offline dictionary learning collects bio-signal samples (e.g., ECG signal samples), applies pre-processing (e.g., DC removal and noise filtering) to the collected bio-signal samples, uses a dictionary learning algorithm to learn signal dictionaries with different resolutions (e.g., signal dictionaries with different dictionary sizes), saves the learned signal dictionaries in the storage device 128, and learns mappings between different scales of signal dictionaries that can be used for dictionary weighting. In addition, offline dictionary learning uses the same bio-signal samples to learn residual dictionaries with different resolutions (e.g., residual dictionaries with different dictionary sizes), learns mappings between different scales of residual dictionaries that can be used for dictionary weighting, and saves the learned residual dictionaries in the storage device 128. For example, a residual dictionary can be learned based on reconstruction residual/error obtained after reconstruction is performed using a signal dictionary. Moreover, the offline dictionary learning collects impairment/noise signal samples (e.g., baseline wandering samples, electrode motion samples, muscle motion samples, and/or 50/60 Hz power line interference samples), applies pre-processing (e.g., DC removal and noise filtering) to the collected impairment/noise samples, uses a dictionary learning algorithm to learn noise dictionaries with different resolutions (e.g., noise dictionaries with different dictionary sizes), learns mappings between different scales of noise dictionaries that can be used for dictionary weighting, and saves the learned noise dictionaries in the storage device 128.

A signal dictionary needed by the online multi-stage reconstruction may be selected from multi-resolution/multi-scale signal dictionaries $D_S$ according to a reconstruction quality requirement. Similarly, a residual dictionary needed by the online multi-stage reconstruction may be selected from multi-resolution/multi-scale residual dictionaries $D_R$ according to the reconstruction quality requirement, and a noise dictionary needed by the online multi-stage reconstruction may be selected from multi-resolution/multi-scale noise dictionaries $D_N$ according to the reconstruction quality requirement. For example, a coarse-resolution dictionary with a small dictionary size is selected for a low reconstruction quality requirement, and a fine-resolution dictionary with a large dictionary size is selected for a high reconstruction quality requirement.

In accordance with the proposed multi-stage reconstruction scheme, the data reconstruction block 131 performs a first-stage reconstruction of a data group according to CS samples of one mega block and a first-stage dictionary, and selectively performs a second-stage reconstruction of the data group according to the CS samples, the first-stage dictionary, and a second-stage dictionary. In other words, the second-stage reconstruction can be bypassed when a criterion is met, thus achieving the required reconstruction quality with fast reconstruction speed.

As shown in FIG. 7, the data reconstruction block 131 performs reconstruction (denoted by "REC") of a data group according to CS samples of a mega block and a signal dictionary, and the quality estimation block 129 performs quality estimation (denoted by "QE") for estimating reconstruction quality associated with reconstruction of the data group to determine if a reconstruction quality requirement is met. For example, the quality estimation (denoted by "QE") may employ the above-mentioned quality estimation strategy which performs sparseness check upon coefficients by, for example, calculating a decay rate of the coefficients, and uses the calculated decay rate as an indication of the reconstruction quality.

When the estimated reconstruction quality does not meet the reconstruction quality requirement, the data reconstruction block 313 combines the signal dictionary and the residual dictionary to obtain an expanded dictionary, and performs reconstruction of the data group again according to CS samples of the mega block and the expanded dictionary (which has the residual dictionary concatenated to the signal dictionary). Next, the data reconstruction block 131 performs scene detection (denoted by "SC") upon reconstructed signal samples to determine if noise (e.g., baseline wandering noise, electrode motion noise, muscle motion noise, or 50/60 Hz power line interference) is present. When the scene detection indicates that noise is present, the data reconstruction block 131 combines the signal dictionary, the residual dictionary and the noise dictionary to obtain an expanded dictionary, and obtains a final reconstruction result by performing reconstruction of the data group again according to CS samples of the mega block and the expanded dictionary (which has the residual dictionary and the noise dictionary concatenated to the signal dictionary). When the scene detection indicates that no noise is present, the data reconstruction block 131 bypasses reconstruction of the data group that is performed using CS samples of the mega block and the expanded dictionary (which has the residual dictionary and the noise dictionary concatenated to the signal dictionary), and obtains a final reconstruction result that is generated from reconstruction performed using CS samples of the mega block and the expanded dictionary (which has the residual dictionary concatenated to the signal dictionary).

When the estimated reconstruction quality meets the reconstruction quality requirement, the data reconstruction block 131 bypasses the reconstruction of the data group that is performed using CS samples of the mega block and the expanded dictionary (which has the residual dictionary concatenated to the signal dictionary). Next, the data reconstruction block 131 performs scene detection upon reconstructed signal samples to determine if noise (e.g., baseline wandering noise, electrode motion noise, muscle motion noise, or 50/60 Hz power line interference) is present. When the scene detection indicates that noise is present, the data reconstruction block 131 combines the signal dictionary and the noise dictionary to obtain an expanded dictionary, and obtains a final reconstruction result by performing reconstruction of the data group again according to CS samples of the mega block and the expanded dictionary (which has the noise dictionary concatenated to the signal dictionary). When the scene detection indicates that no noise is present, the data reconstruction block 131 bypasses reconstruction of the data group that is performed using CS samples of the mega block and the expanded dictionary (which has the noise dictionary concatenated to the signal dictionary), and obtains a final reconstruction result that is generated from reconstruction performed using CS samples of the mega block and the signal dictionary.

The use of the noise dictionary is capable of achieving signal-noise separation. For example, an expanded dictionary derived from combining a signal dictionary $\Psi_{signal}$ and a noise dictionary $\Psi_{noise}$ can be expressed by $[\Psi_{signal} \Psi_{noise}]$. Hence, the matrix equation $Y=\Phi\Psi S$ can be reformulated as $Y=\Phi[\Psi_{signal}\Psi_{noise}][S_{signal}S_{noise}]^T$. After coefficient vectors $S_{signal}$ and $S_{noise}$ are obtained using a proper reconstruction/approximation algorithm, the coefficient vector $S_{noise}$ is discarded, and the coefficient vector $S_{signal}$ is multiplied with the signal dictionary $\Psi_{signal}$ to obtained de-noised reconstructed signal samples. It should be noted that the reconstruction residual can be handled similarly as the impairments. For example, a coefficient vector $S_{residual}$ is discarded, and a coefficient vector $S_{signal}$ is multiplied with a signal dictionary $\Psi_{signal}$ to obtained residual-compensated reconstructed signal samples.

In the embodiment shown in FIG. 7, the initial reconstruction stage uses the signal dictionary, the middle reconstruction stage uses an expanded dictionary created by combining the signal dictionary and the residual dictionary, and the final reconstruction stage uses an expanded dictionary created by combining the signal dictionary, the residual dictionary and the noise dictionary or an expanded dictionary created by combining the signal dictionary and the noise dictionary. However, this is for illustrative purposes only, and is not meant to be a limitation of the present invention. Alternatively, the initial reconstruction stage may use the signal dictionary, the middle reconstruction stage may use an expanded dictionary created by combining the signal dictionary and the noise dictionary, and the final reconstruction stage may use an expanded dictionary created by combining the signal dictionary, the noise dictionary and the residual dictionary or an expanded dictionary created by combining the signal dictionary and the residual dictionary. In other words, the order of residual handling and impairment handling can be changed, depending upon the actual design considerations.

As mentioned above, the quality estimation result can be used to control enabling of a next reconstruction stage that can be used for improving accuracy of reconstructed signal samples. In some embodiments of the present invention, the quality estimation result may be used to control enabling of online dictionary update of a currently used signal dictionary. For example, the data reconstruction block 131 uses the estimated reconstruction quality to check the dictionary fitness. When the estimated reconstruction quality obtained by the quality estimation block 129 does not meet the reconstruction quality requirement, the request control block 130 requests new CS samples from the source electronic device 10, and the data reconstruction block 131 performs online dictionary update upon the signal dictionary according to the new CS samples. A reasonable amount of new CS samples is required to achieve re-fitting of an existing signal dictionary. However, re-fitting of the existing signal dictionary is still faster than learning of a new signal dictionary.

Figure 8:
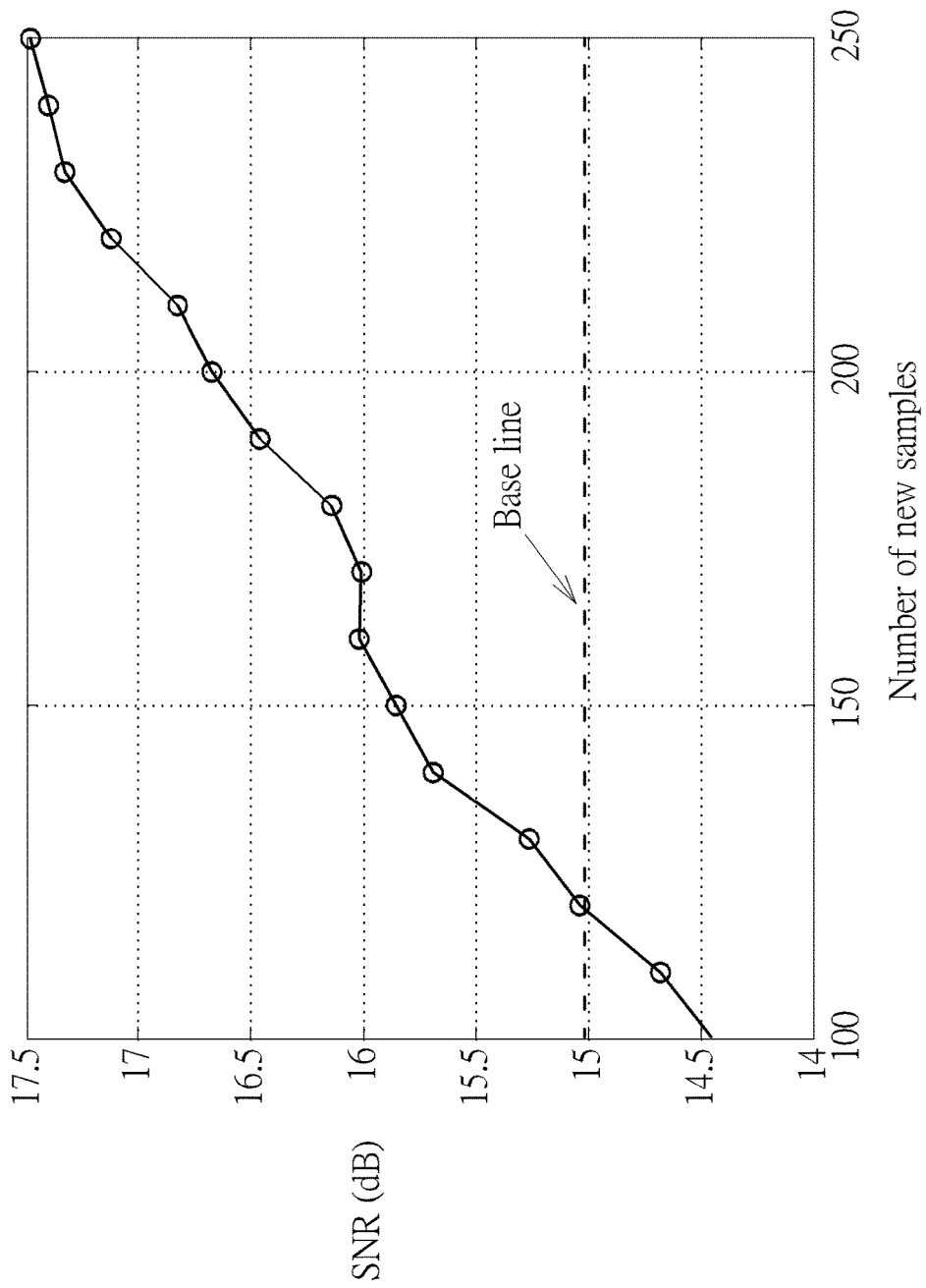
FIG. 8 is a diagram illustrating a relation between the reconstruction quality and the number of new CS samples used by online dictionary update according to an embodiment of the present invention.

FIG. 8 is a diagram illustrating a relation between the reconstruction quality and the number of new CS samples used by online dictionary update according to an embodiment of the present invention. A common dictionary that is obtained by offline dictionary learning may be used as a start point. The base line of SNR is 15 dB. Hence, the reconstruction quality requirement is met when SNR≥15 dB. As shown in FIG. 8, using the common dictionary is unable to meet the reconstruction quality requirement. After the common dictionary is updated by a reasonable amount of new CS samples, using the updated dictionary is able to meet the reconstruction quality requirement. In other words, the reconstruction quality can be improved by performing online dictionary update upon the dictionary.

When the variable rate transmission scheme is employed by the source electronic device 10, the reconstruction quality can be improved by transmitting more CS samples in one mega block to the destination electronic device 20. When the feature of online dictionary update is enabled, an offline learned dictionary can be online updated for adapting to new observations, such that the reconstruction quality can be improved by using the updated dictionary. In some embodiment of the present invention, the proposed quality control strategies, including the variable rate transmission and the online dictionary update, may be both used for reconstruction quality improvement.

Figure 9:
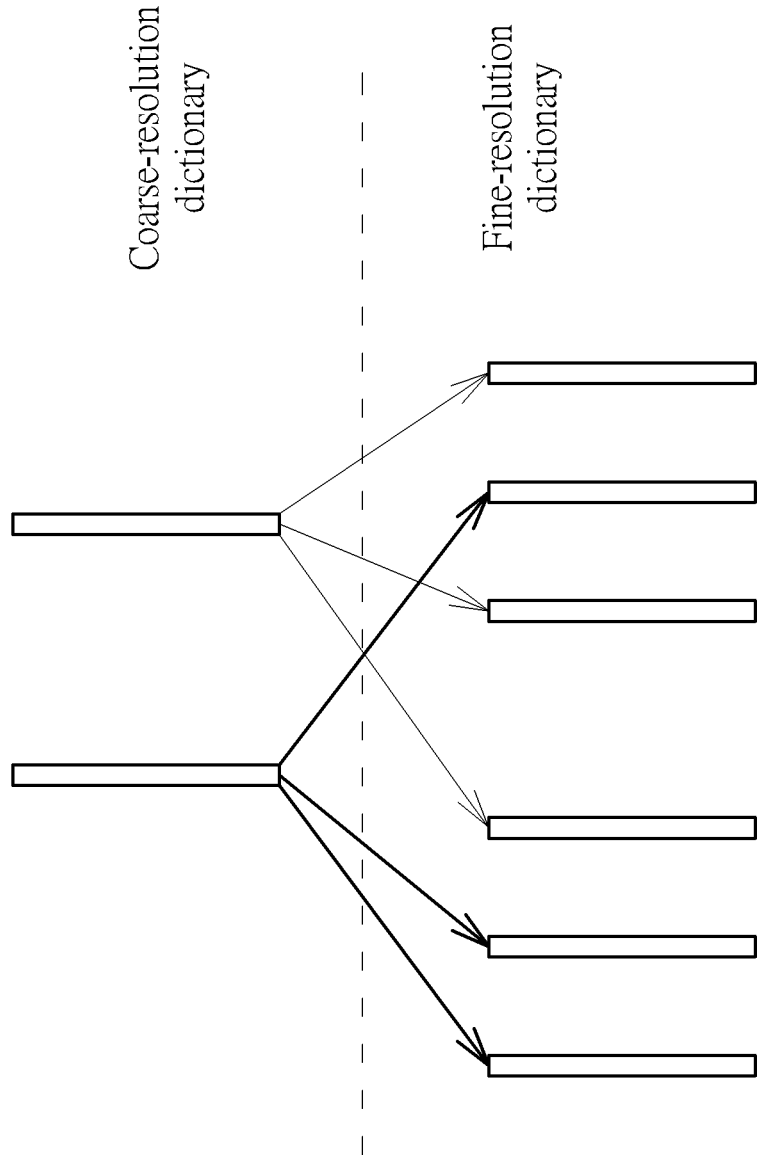
FIG. 9 is a diagram illustrating dictionary weighting of a coarse-resolution dictionary and a fine-resolution dictionary according to an embodiment of the present invention.

The multi-resolution/multi-scale signal dictionaries $D_S$, multi-resolution/multi-scale residual dictionaries $D_R$, and multi-resolution/multi-scale noise dictionaries $D_N$ may be obtained by offline dictionary learning. As mentioned above, the offline dictionary learning also learns mappings of different scales of dictionaries. For example, a proper mapping between a coarse-resolution dictionary with a smaller dictionary size and a fine-resolution dictionary with a larger dictionary size is also learned by the offline dictionary learning and recorded in the storage device 128. In some embodiments of the present invention, the data reconstruction block 131 performs dictionary weighting upon the coarse-resolution dictionary and the fine-resolution dictionary by identifying specific atoms in the coarse-resolution dictionary and then using the specific atoms to emphasize correlated atoms in the fine-resolution dictionary via proper weighting/blending of these selected atoms of coarse-resolution signal dictionary and fine-resolution dictionary, as illustrated in FIG. 9. Hence, parts of the fine-resolution dictionary will be initialized with high weights directed by the coarse-resolution dictionary. With this proper initialization of weights, the reconstruction using fine dictionary not only results in better quality but also faster convergence speed compared to the un-weights ones, based on the same reconstruction algorithm.

Compressive sensing is based on the concept of random projection (i.e., random sampling) which compresses information of the entire block into a small number of measurement values. However, for certain bio-signals, there exist some special feature points. For example, an ECG signal has P, Q, R, S, T points. Due to inherent characteristics of random sampling, random sampling does not provide any guarantee on those important feature points. That is, when a signal segment of the bio-signal has important feature points, the associated CS samples through random projection may not preserve all information regarding these important feature points. To solve this problem, the present invention proposes using feature point detection to find feature point samples and transmitting at least a portion (i.e., part or all) of the found feature point samples to the destination electronic device 20. Random sampling and feature point sampling can be combined into a single framework to achieve a better reconstruction result. The CS samples and the feature point sample(s) can be jointly considered by the CS reconstruction to produce a more accurate approximation result, where each feature point sample acts as a point constraint for the CS reconstruction.

The sample generation block 117 performs compressive sensing to generate CS samples corresponding to a signal segment of the bio-signal within a time window, and outputs the CS samples to the destination electronic device 20 via the TX circuit 114. When the variable rate transmission scheme is enabled, the transmitted CS samples may be a portion of CS samples of one mega block. When the feature point detection is also enabled, the feature point detection circuit 112 uses a feature point detection algorithm to detect at least one feature point sample associated with at least one feature point of the signal segment, and outputs at least one feature point sample to the destination electronic device 20 via the TX circuit 114. Since the sample generation block 117 performs compressive sensing in the digital domain, the feature point detection circuit 112 can also perform the feature point detection in the digital domain to take advantage of the digital compressive sensing design. Hence, a simple feature point detection algorithm, such as a one-pass algorithm, can be employed to detect feature points. This can reduce the hardware complexity. In addition, weighting may be applied to feature point samples before the feature point samples are transmitted, where large weighting makes the point constraints more effective.

The data reconstruction block 131 receives CS samples corresponding to the signal segment of the bio-signal and at least one feature point sample associated with at least one feature point of the signal segment of the bio-signal from the source electronic device 10 via the RX circuit 122, and performs reconstruction of a data group according to the CS samples and at least one feature point sample, where at least one feature point sample acts as at least one point constraint for reconstruction of the data group. The point constraints can be absorbed into a generalized CS formation with weighting on the feature point samples. Concerning the matrix equation $Y=\Phi\Psi S$, the measurement vector Y becomes $[Y\ \beta\times(p_1)\ \ldots\ \beta\times(p_N)]^T$ when point constraints are added, where $p_1$-$p_N$ are feature point samples, and $\beta$ is the feature point weighting factor. It should be noted that the measurement matrix $\Phi$ and the dictionary $\Psi$ should be properly expanded after additional samples (i.e., feature point samples) are added to the measurement vector Y. An example of expanded measurement matrix $\Phi$ and expanded dictionary $\Psi$ is provided below for illustrative purpose.

$$\Phi = \begin{bmatrix} \Phi_{11} & \Phi_{12} & \ldots & \ldots & \Phi_{1N} \\ \ldots & \ldots & \ldots & \ldots & \ldots \\ \Phi_{M1} & \Phi_{M2} & \ldots & \ldots & \Phi_{MN} \\ \beta & 0 & \ldots & \ldots & 0 \\ \ldots & \ldots & \ldots & \ldots & \ldots \\ 0 & \ldots & \beta & \ldots & 0 \end{bmatrix}$$

$$\Psi = \begin{bmatrix} \Psi_{11} & \ldots & \Psi_{1L} & 1 & \ldots & 0 \\ \Psi_{21} & \ldots & \Psi_{2L} & 0 & \ldots & \ldots \\ \ldots & \ldots & \ldots & \ldots & \ldots & 1 \\ \ldots & \ldots & \ldots & \ldots & \ldots & \ldots \\ \Psi_{N1} & \ldots & \Psi_{NL} & 0 & \ldots & 0 \end{bmatrix}$$

Figure 10:
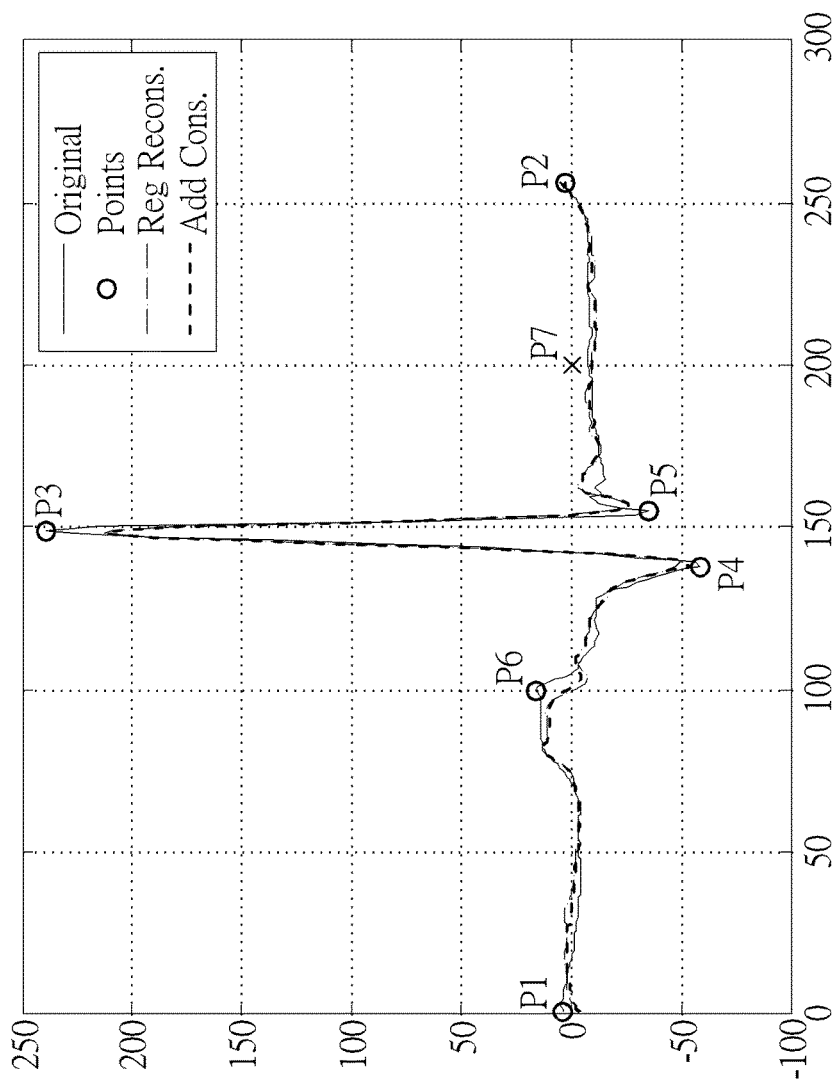
FIG. 10 is a diagram illustrating an original signal, a reconstructed signal generated from regular reconstruction with no additional point constraints and a reconstructed signal generated from reconstruction with additional point constraints according to an embodiment of the present invention.
Figure 11:
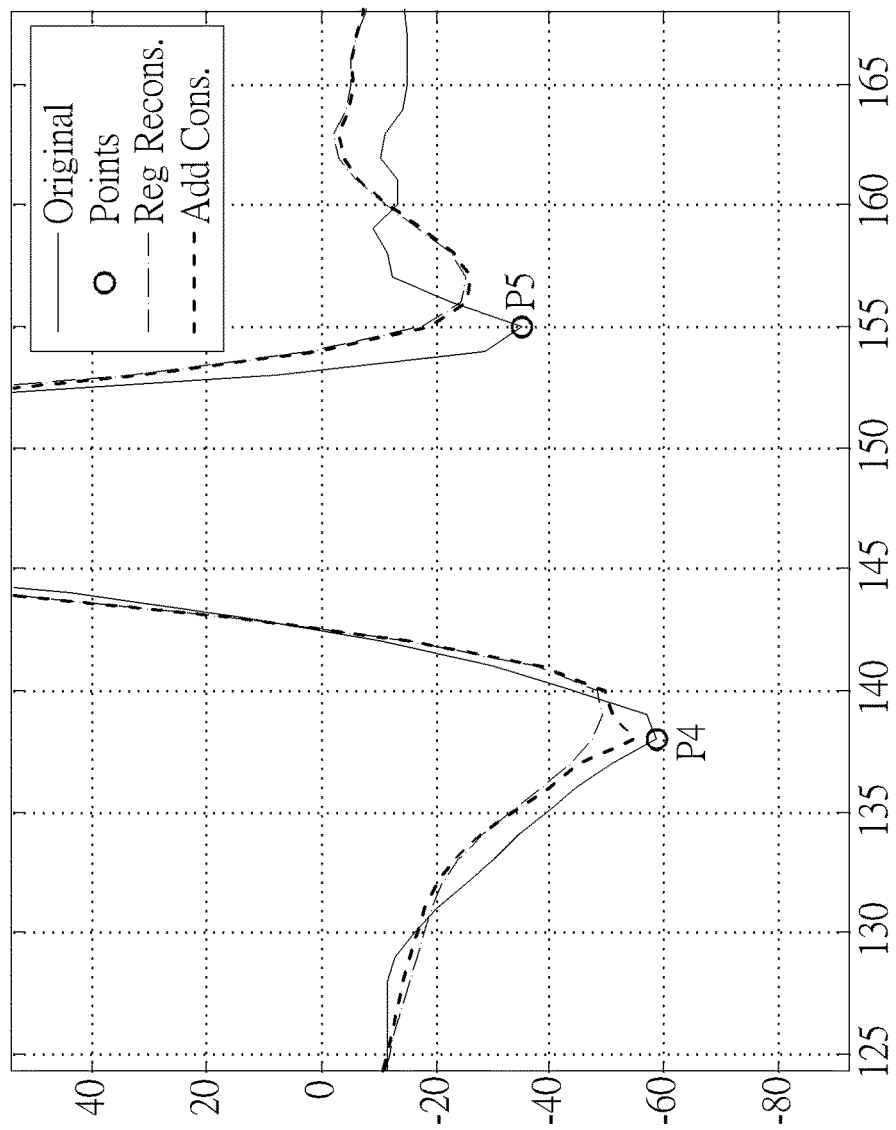
FIG. 11 is a diagram illustrating an enlarged view of middle parts of the signals shown in FIG. 10.

Adding point constraints can enforce better approximation around their neighborhoods. FIG. 10 is a diagram illustrating an original signal, a reconstructed signal generated from regular reconstruction with no additional point constraints and a reconstructed signal generated from reconstruction with additional point constraints according to an embodiment of the present invention. FIG. 11 is a diagram illustrating an enlarged view of middle parts of the signals shown in FIG. 10. The original signal has a plurality of important feature points, such as a left end point P1, a right end point P2, a global maximum point P3, a left local minimum point P4 around P3, a right local minimum point P5 around P3, a local maximum point P6 between P1 and P4, and a local maximum point P7 between P5 and P2. It should be noted that not all points are present all the time.

In this example shown in FIG. 10, the feature point P7 does not exist. Compared to the reconstructed signal generated from regular reconstruction with no additional point constraints, the reconstructed signal generated from reconstruction with additional point constraints has better approximation around the feature points. In addition, the point constraints are usually more effective for a large CR, and are especially useful to enforce continuality between two neighboring signal blocks. When the multi-stage reconstruction scheme is employed by the destination electronic device 20, the point constraints can work together with one reconstruction stage using a signal dictionary or another reconstruction stage using an expanded dictionary that is composed of a signal dictionary and a residual dictionary.

The feature point detection result obtained by the feature point detection circuit 112 also provides information of complexity of the bio-signal. For example, the number of detected feature point samples included in the feature point detection result can be used to predict the signal complexity. When the number of detected feature point samples is large, the bio-signal may have high complexity. When the number of detected feature point samples is small, the bio-signal may have low complexity. Hence, the feature point detection result may be used by the processing circuit 108 to control the compression ratio. For example, when the variable rate transmission scheme is employed by the source electronic device 10, the TX control block 118 further refers to the feature point detection result to set the size of the first portion of CS samples of one mega block that is initially transmitted to the destination electronic device 20. When the feature point detection result indicates that the signal has low complexity, the size of the first portion of CS samples of one mega block $$\frac{1}{A} \cdot S_{MB}$$

can be set by a small value $$\left(\text{e.g., } \frac{1}{8} \cdot S_{MB}\right).$$

When the feature point detection result indicates that the signal has high complexity, the size of the first portion of CS samples of one mega block $$\frac{1}{A} \cdot S_{MB}$$

can be set by a large value $$\left(\text{e.g., } \frac{1}{4} \cdot S_{MB}\right).$$

In this way, the latency caused by feedback from the destination electronic device 20 can be reduced or avoided.

As mentioned above, the feature point detection result obtained by the feature point detection circuit 112 can provide information of the complexity of the bio-signal. Hence, the number of detected feature point samples included in the feature point detection result may also be used to predict the reconstruction quality at the destination electronic device 20. When the number of detected feature point samples is large, the bio-signal may have high complexity, and the reconstruction quality estimated at the destination electronic device 20 may be low. When the number of detected feature point samples is small, the bio-signal may have low complexity, and the reconstruction quality estimated at the destination electronic device 20 may be high. Hence, the feature point detection result may be used by the feature point detection circuit 112 to control the number of feature point samples transmitted to the destination electronic device 20. In other words, the feature point detection circuit 112 dynamically changes the number of feature point samples transmitted to the destination electronic device 20 according to a feature point detection result associated with each signal segment of the bio-signal.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An electronic device comprising:
  a transmit circuit; and
  a processing circuit, arranged to output a first portion of compressive sensing (CS) samples corresponding to a signal segment to another electronic device via the transmit circuit, and further arranged to selectively output a second portion of the CS samples corresponding to the signal segment to said another electronic device via the transmit circuit according to a response of said another electronic device.

2. The electronic device of claim 1, further comprising:
  a receive circuit;
  wherein when the processing circuit receives a request for more CS samples corresponding to the signal segment from said another electronic device via the receive circuit, the processing circuit outputs the second portion of the CS samples corresponding to the signal segment to said another electronic device via the transmit circuit; and when the processing circuit does not receive the request from said another electronic device via the receive circuit, the processing circuit does not output the second portion of the CS samples corresponding to the signal segment to said another electronic device via the transmit circuit.

3. The electronic device of claim 2, further comprising:
  a storage device;
  wherein the processing circuit is further arranged to dump the second portion of the CS samples corresponding to the signal segment into the storage device; when the request is not received by the processing circuit, the second portion of the CS samples corresponding to the signal segment is kept in the storage device; and when the request is received by the processing circuit, the second portion of the CS samples corresponding to the signal segment is read from the storage device and then transmitted to said another electronic device.

4. The electronic device of claim 1, further comprising:
  a feature point detection circuit, arranged to detect at least one feature point associated with the signal segment to generate a feature point detection result;
  wherein the processing circuit is further arranged to refer to the feature point detection result to set a size of the first portion of the CS samples that is transmitted to the another electronic device.

5. An electronic device comprising:
a receive circuit; and
a processing circuit, arranged to receive a first portion of compressive sensing (CS) samples corresponding to a signal segment from another electronic device via the receive circuit, and further arranged to selectively request a second portion of the CS samples corresponding to the signal segment from said another electronic device according to a reconstruction quality requirement.

6. The electronic device of claim 5, wherein the processing circuit is further arranged to perform reconstruction of a data group according to the first portion of the CS samples corresponding to the signal segment, and estimate reconstruction quality associated with the reconstruction of the data group to determine if the reconstruction quality requirement is met.

7. The electronic device of claim 6, wherein the reconstruction quality is estimated by performing sparseness check upon coefficients in a sparse basis that are found by the reconstruction of the data group.

8. The electronic device of claim 7, wherein the sparseness check comprises calculating a decay rate of the coefficients, and the decay rate is used as an indication of the reconstruction quality.

9. The electronic device of claim 6, further comprising:
a transmit circuit;
wherein when the estimated reconstruction quality does not meet the reconstruction quality requirement, the processing circuit issues a request for the second portion of the CS samples corresponding to the signal segment to said another electronic device via the transmit circuit, and when the estimated reconstruction quality meets the reconstruction quality requirement, the processing circuit does not issue the request for the second portion of the CS samples corresponding to the signal segment to said another electronic device via the transmit circuit.

10. An electronic device comprising:
a storage device, arranged to store a plurality of dictionaries, including at least one first-stage dictionary and at least one second-stage dictionary; and
a processing circuit, arranged to perform a first-stage reconstruction of a data group according to compressive sensing (CS) samples corresponding to a signal segment and a first-stage dictionary selected from said at least one first-stage dictionary, and further arranged to selectively perform a second-stage reconstruction of the data group according to the CS samples corresponding to the signal segment, the first-stage dictionary, and a second-stage dictionary selected from said at least one second-stage dictionary.

11. The electronic device of claim 10, wherein the first-stage dictionary is a signal dictionary, and the second-stage dictionary is a residual dictionary.

12. The electronic device of claim 11, wherein the processing circuit is further arranged to estimate reconstruction quality associated with the first-stage reconstruction of the data group to determine if a reconstruction quality requirement is met; when the estimated reconstruction quality does not meet the reconstruction quality requirement, the processing circuit performs the second-stage reconstruction of the data group; and when the estimated reconstruction quality meets the reconstruction quality requirement, the processing circuit bypasses the second-stage reconstruction of the data group.

13. The electronic device of claim 10, wherein the first-stage dictionary is a signal dictionary, and the second-stage dictionary is a noise dictionary.

14. The electronic device of claim 13, wherein the processing circuit is further arranged to perform scene detection to determine if noise is present; when the scene detection indicates that noise is present, the processing circuit performs the second-stage reconstruction of the data group; and when the scene detection indicates that noise is not present, the processing circuit bypasses the second-stage reconstruction of the data group.

15. The electronic device of claim 10, wherein said at least one first-stage dictionary or at least one second-stage dictionary comprises a first dictionary with a first resolution and a second dictionary with a second resolution finer than the first resolution; and one of the first dictionary and the second dictionary is selected for reconstruction of the data group according to a reconstruction quality requirement.

16. The electronic device of claim 15, wherein the processing circuit is further arranged to perform dictionary weighting upon the first dictionary and the second dictionary by identifying specific atoms in the first dictionary and using the specific atoms to emphasize correlated atoms in the second dictionary.

17. The electronic device of claim 10, wherein the processing circuit is further arranged to estimate reconstruction quality associated with the first-stage reconstruction of the data group to determine if a reconstruction quality requirement is met; when the estimated reconstruction quality does not meet the reconstruction quality requirement, the processing circuit is further arranged to request new CS samples from said another electronic device, and perform online dictionary update upon the first-stage dictionary according to the new CS samples.

18. An electronic device comprising:
a transmit circuit;
a processing circuit, arranged to perform compressive sensing (CS) to generate CS samples corresponding to a signal segment, and output at least a portion of the CS samples corresponding to the signal segment to another electronic device via the transmit circuit; and
a feature point detection circuit, arranged to detect at least one feature point sample associated with at least one feature point of the signal segment, and output said at least one feature point sample to said another electronic device via the transmit circuit.

19. The electronic device of claim 18, wherein the feature point detection circuit dynamically change a number of feature point samples transmitted to said another electronic device according to a feature point detection result associated with each signal segment.

20. An electronic device comprising:
a receive circuit; and
a processing circuit, arranged to receive at least a portion of compressive sensing (CS) samples corresponding to a signal segment and at least one feature point sample associated with at least one feature point of the signal segment from another electronic device via the receive circuit, and perform reconstruction of a data group according to said at least a portion of the CS samples and said at least one feature point sample.

* * * * *